United States Patent [19]

Hinkle

[11] Patent Number: 4,896,666
[45] Date of Patent: Jan. 30, 1990

[54] FACE MASK ASSEMBLY AND PACIFIER

[76] Inventor: Allen J. Hinkle, Hardy Hill Rd., Lebanon, N.H. 03766

[21] Appl. No.: 70,563

[22] Filed: Jul. 6, 1987

Related U.S. Application Data

[63] Continuation of Ser. No. 688,611, Jan. 3, 1985, abandoned.

[51] Int. Cl.⁴ .............................................. A61M 15/00
[52] U.S. Cl. ........................... 128/202.13; 128/207.27; 128/206.29; 128/205.75; 128/203.29; 606/235
[58] Field of Search .................. 128/136, 150, 200.24, 128/200.28, 201.26, 202.13, 202.16, 203.29, 204.18, 205.25, 206.29, 207.14, 359, 360, 728, 774, 776, 777; 604/54, 77; 215/11 R–11 D; 432/86, 91, 93, 146

[56] References Cited

U.S. PATENT DOCUMENTS

| | | | |
|---|---|---|---|
| 146,730 | 1/1974 | Vickers | 128/207.14 |
| 2,383,649 | 8/1945 | Heidbrink | 128/206.29 |
| 2,743,727 | 5/1956 | Griesinger | 178/360 |
| 3,426,755 | 2/1964 | Clegg | 604/77 |
| 3,964,489 | 6/1978 | Kesselring | 128/360 |
| 4,192,307 | 3/1980 | Baer | 128/360 |
| 4,193,407 | 3/1980 | Edmark | 128/360 |
| 4,402,316 | 9/1983 | Gadberry | 128/206.24 |
| 4,503,851 | 3/1985 | Braunroth | 128/206.19 |
| 4,513,741 | 4/1985 | Demi | 128/206.29 |
| 4,520,809 | 6/1985 | de Greef et al. | 128/207.18 |
| 4,545,378 | 10/1985 | Chrones | 128/359 |

FOREIGN PATENT DOCUMENTS

| | | | |
|---|---|---|---|
| 720046 | 4/1942 | Fed. Rep. of Germany | 128/202.13 |
| 23063 | 4/1962 | German Democratic Rep. | 128/206.29 |
| 1118738 | 7/1968 | United Kingdom | 128/389 |
| 1135102 | 11/1968 | United Kingdom | 128/202.13 |

*Primary Examiner*—Max Hindenburg
*Assistant Examiner*—K. M. Reichle
*Attorney, Agent, or Firm*—Schiller, Pandiscio & Kusmer

[57] ABSTRACT

A face mask assembly comprises a face mask and a pacifier constructed to be easily attached to the face mask. The pacifier is provided with a novel construction for use with either the face mask for pre-operative and operative procedures, or a shield for pre- and post-operative care.

16 Claims, 2 Drawing Sheets

FACE MASK ASSEMBLY AND PACIFIER

CROSS-REFERENCE TO RELATED APPLICATION

This application is a continuation of application Ser. No. 688,611, filed Jan. 9, 1985, now abandoned.

BACKGROUND OF THE INVENTION

The present invention relates generally to an improved face mask assembly particularly adapted for use with infants and, more particularly, to an improved medical face mask assembly including a detachable pacifier.

Normal operative procedures require a patient to fast prior to surgery in order to reduce the problems associated with regurgitated material during an operation. As a consequence, patients are often hungry and thirsty when anesthesia is induced. Often therefore, many patients, such as infants, will cry during pre-operative procedures making anesthesia induction difficult. Many children will suck vigorously at the edge of a standard face mask as the anesthesiologist attempts to place the mask over infants' faces. While such suckling quiets a child, it will often prevent the face mask from being properly positioned on the child's face and, therefore, prevent a tight seal from being formed around the edge of the mask in order to perform a smooth and rapid inhalational induction of an anesthetic gas. Additionally, the smell and/or taste of such masks may be unappealing and therefore less acceptable to a child. Accordingly, many pediatric anesthesiologists have resorted to giving a pacifier to the infant prior to inducing the anesthesia. Giving a pacifier to the infant, however, usually requires the anesthesiologist to use a larger face mask, which increases the dead space (the term "dead space" being defined as the volume of space which can contain and trap a potentially unacceptably large quantity of user-exhausted carbon dioxide that can be rebreathed by a patient and includes anatomical areas, such as the oropharynx and trachea, as well as the physical space between the interior of a medical face mask and the portion of the surface area of the face the mask covers) and makes it more difficult to maintain a tight fit of the mask to the face. Increasing the dead space can lead to respiratory complications. Where an infant is provided with a separate pacifier during anesthesia induction, should it be necessary to perform a ventilatory procedure, the mask and pacifier often have to be removed in order that proper suctioning can be accomplished.

A prior art face mask is shown in U.S. Pat. No. 1,000,706 U.S. Pat. Nos. 1,476,194 and 3,139,088 illustrates inhaling devices including tubes adapted to be inserted in the mouth. U.S. Pat. Nos. 2,521,084, 3,809,079 and 4,470,413 show face mask assemblies with air ways adapted to be inserted into the mouth of a patient. None of these devices are satisfactory in calming infant patients during anesthesia induction. While pacifier assemblies are certainly known (see U.S. Pat. No. 2,612,165) none are adapted to be attached to medical face masks, such as those used for anesthesia induction or respiration functions.

It is a general object of the present invention to provide an improved face mask assembly which reduces or overcomes the above-noted problems.

A more specific object of the present invention is to provide an improved face mask assembly designed to promote suckling and quiet the patient while providing an adequate passageway for transporting air or an anesthetic gas to a patient.

Another specific object of the present invention is to provide an improved face mask assembly including a detachable pacifier and designed so as to more easily provide a tight seal around the face mask.

And another specific object of the present invention is to provide an improved face mask usable with or without a detachable pacifier.

Still another object of the present invention is to provide an improved face mask assembly including a pacifier attachable to a face mask in such a manner so as to prohibit oral entrainment or swallowing by the patient of all or portions of the assembly.

Yet another specific object of the present invention is to provide a face mask assembly including an attachable pacifier incorporated with a flavoring or fragrance so as to enhance the acceptance of the assembly by an infant patient.

And still another specific object of the present invention is to provide an improved face mask assembly including an attachable pacifier in which a ventilation procedure can be performed without removing the assembly from the patient.

And yet another specific object of the present invention is to reduce the physical dead space within a face mask, as well as the anatomical dead space in the patient, when the face mask is properly positioned on a patient's face.

And still another specific object of the present invention is to provide an improved pacifier constructed to be easily attached to a face mask for pre-operative and operative procedures, and used with an attachable shield for pre- and post-operative care.

SUMMARY OF THE INVENTION (1) a face mask assembly comprising, in combination: a face mask and a pacifier constructed to be easily attached to or detached from the face mask; and (2) an novel pacifier designed to be used either with a medical face mask for pre-operative and operative procedures, or a shield for pre- and post-operative care.

Other objects of the invention will in part be obvious and will in part appear hereinafter. The invention, accordingly, comprises the product possessing the features, properties and relation of components which are exemplified in the following detailed disclosure, and the scope of the application of which will be indicated by the claims.

DESCRIPTION OF THE DRAWINGS

For a fuller understanding of the nature and objects of the present invention, reference should be had to the following detailed description taken in connection with the accompanying drawings, wherein.

DETAILED DESCRIPTION OF THE INVENTION

Figure 1:
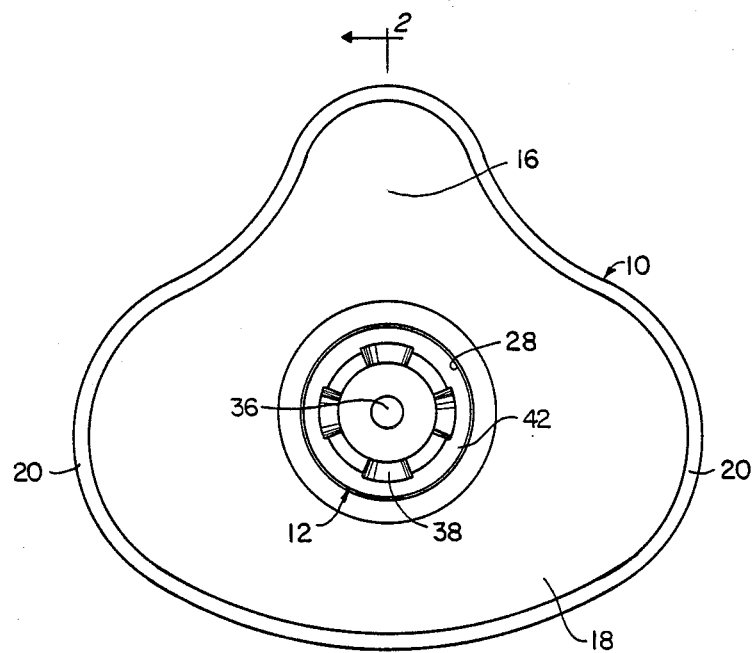
FIG. 1 is a front view of the preferred embodiment of the face mask assembly of the present invention.
Figure 2:
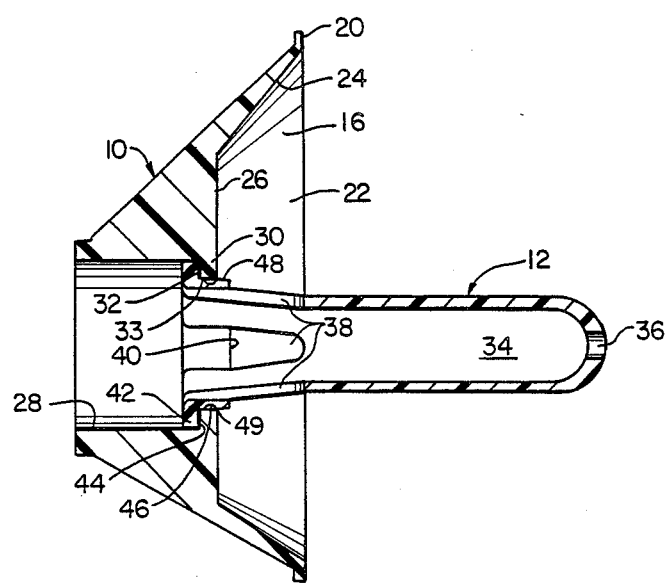
FIG. 2 is a longitudinal cross-sectional view taken along line 2—2 of FIG. 1.

The assembly of the present invention includes the medical faces mask 10 (shown in FIGS. 1-2) and the pacifier 12 (shown in FIGS. 1-4) detachably secured to the face mask 10. The pacifier is constructed so that it can also be secured to the shield 14 (shown in FIGS. 3-4) for pre- and post-operative care.

The face mask 10 is generally contoured to extend over at least the nose and mouth of the wearer of the mask so that the edges of the mask tightly contact the face of the wearer. Although the preferred embodiment is described as being primarily useful with patients who are infants, it can also be used with older children as well as adults. Accordingly, the actual size of the mask can vary to accommodate different age groups and the shape of the mask also may be varied to accommodate different types of facial contours, e.g., wide and narrow cheek bones, small and large chins, etc. The face mask 10 includes the nose cover portion 16 and mouth and cheek cover portion 18, portions 16 and 18 being defined by the outer edge rim 20 extending around the periphery of the back of the face mask. The rim 20 preferably is rounded smooth to avoid sharp edges, and if desired provided with a cushion material (not shown), so as to comfortably engage the face of the wearer while maintaining an air-tight seal. The cover portions 16 and 18 on the rear side of the mask create a hollow space 22, defined by the inclined inner surfaces 24 and inner wall 26. Space 22 receives the portions of the face covered by the face mask and defines with the face a confined air space which is a part of the dead space. As is well-known, the dead space should be minimized, especially where the mask is used for anesthesia induction so as to minimize the rebreathing of expired carbon dioxide.

The mask 10 also includes an opening 28, approximately centered in the mouth and cheek cover portion 18 of the mask and extending from the front of the mask through the inner wall 26 opposite the location of where the mouth is located when the mask is worn by a patient. The opening is preferably of a cylindrical cross-section for receiving, for example, a face mask connector (not shown) which may or may not be provided with an expiratory valve, as is well-known. Although not shown, a metal brushing may be inserted in the opening 28 for accommodating the connector and a multiprong head strap hook may be provided at the front of the mask around the opening for connecting a head strap so that the mask can be held closely in place. To the extent described, the mask is similar to many currently commercially-available face masks. If desired, when for example the pacifier is not needed, the face mask can be used alone in the same manner as comparable prior art face masks.

The mask 10 is modified in accordance with the present invention to include an inward radially-directed annular flange 30 formed at the back end of opening 28 so that the pacifier 12 can be attached. Flange 30 includes the annular shoulder 32 disposed in a plane parallel to the inner wall 26 and the cylindrical surface 33 coaxially disposed with the center axis of opening 28.

The pacifier 12 is an elongated, integrally-formed element. The pacifier is made so as to define the non-collapsable passageway 34. The pacifier also includes a hole 36, preferably at its tip, communicating with passageway 34. The pacifier is also preferably provided with at least one aperture 38 in the wall of the pacifier, between the base portion of the pacifier and the tip at a position so that (1) the aperture 38 communicates with the space 22 of the mask 10 when the pacifier is attached to the mask, and (2) gas provided to the mask through opening 28 into the passageway 34 of the pacifier 12 will also pass through the aperture 38 into the space 22. As shown, the preferred embodiment of the pacifier includes four such apertures equiangulary disposed around the elongated axis of the pacifier. The base of the pacifier is open and is provided with coupling means preferably in the form of a ring 40 circumferentially disposed around and integrally formed as the base of the pacifier, for attaching the pacifier to the mask 10 or shield. 14 Ring 40 includes the annular outwardly directed radial flange 42 having an annular shoulder 44. The flange 42 has a diameter approximately the same as opening 28, but larger than cylindrical surface 33 so that the flange 42 will freely slide axially in opening 28 but will be restrained by flange 30 of the mask when pacifier 12 is secured to the mask 10. An annular groove 46 is disposed on the outer surface of ring 40 of the pacifier adjacent the shoulder 14. An annular lip 48 also radially extends out from the outer surface of ring 40 of pacifier 12 and is disposed adjacent the groove 46 so as to form an annular channel between the lip 48 and flange 42. The lip 48 has a smaller outside diameter than the outside diameter of the flange 42, and is provided with a beveled outer edge, larger in diameter at the base end of the lip so as to form the edge tip 49, for reasons which will be more evident hereinafter.

The pacifier 12 can be easily and securely attached to the mask 10 by sliding the pacifier 12 tip end first through the front of opening 28, pushing the pacifier through until the annular shoulder 44 of the flange 42 of the ring 40 contacts the annular shoulder 32 of flange 30 of mask 10. The lip 48 will engage the inner cylindrical surface 33 of flange 30 as the pacifier is pushed, but will easily slide through due to the beveled shape of the outer edge of the lip 48. The edge tip 49 formed at the base end of the lip 48 will engage the inner wall 26 of mask 10 at the opening of the flange 30 helping to lock the pacifier in place such that the flange 30 is disposed in the annular channel provided between flange 42 and lip 48. The annular groove 46 provides some flexibility between the flange 42 and lip 48 so that the pacifier can be detached from the mask by merely pushing the pacifier in the opposite direction, i.e., back out the front of opening 28. With sufficient axial force the lip 48 will disengage wall 26 of the mask 10 and be forced through the opening of flange 30.

When used with the mask 10, the pacifier 12 is positioned to extend from the interior of the mask 12 and is capable of being inserted into the mouth of the wearer so as to occupy a substantial portion of the anatomical space of the oropharynx and depress the tongue of the wearer of the mask. An anesthetic gas can be introduced through the opening 28 where it will pass through passageway 34 of the pacifier through apertures 38 into the air space 22 so that the wearer can breathe the gas through the nose. Thus, the mask will be more readily received and easily positioned with respect to an infant when anesthesia is induced. Should it be necessary to ventilate while the mask is in position, the entire mask can be removed, or if desired, a catheter can be inserted through opening 28 of the mask and through passageway 34 so that the end of the catheter is positioned between the apertures 38 and hole 36 and suction can be provided through hole 36 at the tip. It should be appreciated that the face mask assembly can be used for any application where the mask 10 is to be placed on the patient's face, including, but not limited to anasthesia induction and respiration functions.

Figure 3:
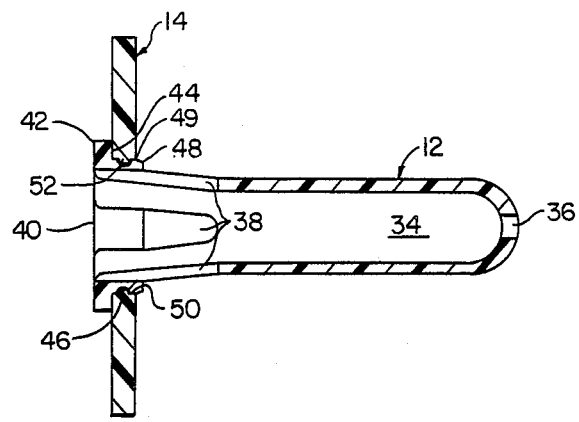
FIG. 3 is a longitudinal cross-sectional view of the preferred embodiment of the pacifier-shield assembly of the present invention.
Figure 4:
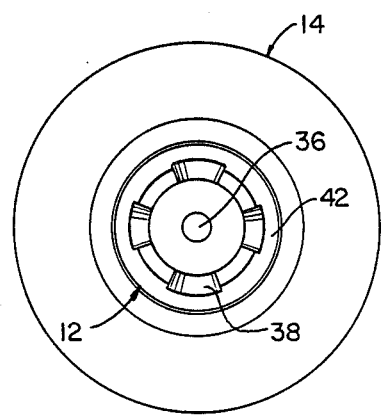
FIG. 4 is a front view of the assembly of FIG. 3.

As shown in FIGS. 3 and 4, the pacifier 12 can also be secured to a shield 14 for pre- and post-operative care. The shield is provided with an aperture 50 defined at least in part by an inner lip 52 of reduced thickness for extending in the groove 46 between the flange 42 and lip 48 when the pacifier is attached. The aperture 50 has approximately the same diameter as the lip 48 and is smaller in diameter than that of the flange 42 of the ring 40 of pacifier 12 so that the pacifier can be easily pushed through the aperture 50 in the same manner so that the pacifier is securely held in place. The shape of the shield may take any shape with an annular disk shape being preferred since no sharp edges are provided.

The mask 10, pacifier 12 and shield 14 may be made of any biologically-compatible and structurally-durable material, such as a polyethylene or a polyvinyl chloride. The pacifier 12 should be made of a material strong enough so that when the pacifier is inserted in the mouth and sucked on, the passageway 34 will remain non-collapsible, clearly distinguishing it from standard feeding nipples. Preferably, at least the pacifier are provided with a fragrance and/or taste which is appealing to the patient to make it more acceptable, for example, to infants. The fragrance can be provided, for example, by adding 6% by weight of a fragrance concentrate (manufactured under the trademark Polyiff and trade designation 17402-00388 Tutti Fruity by International Flavors and Fragrances Inc. of Hazlet, NJ) to a polyvinyl chloride matrix, and forming the various components by injection molding.

The mask 10, pacifier 12 and shield 14 provide several advantages. The mask assembly is designed to promote suckling and quiet the patient while providing an adequate passageway for transporting air or an anesthetic gas to a patient. The mask can be used with or without the pacifier. When the pacifier is used with the mask a tight seal can easily be achieved around the face mask even with the smallest of infants. The pacifier can be secured to the face mask in such a manner so as to prohibit excessive oral entrainment or swallowing by the patient of all or portions of the assembly. The pacifier may be provided with a flavoring or fragrance so as to enhance patient acceptance of the assembly. The mask and pacifier assembly is designed to easily perform a ventilation procedure without removing the assembly from the patient. The design of the assembly is such that the smallest applicable face mask can be used with each patient. Thus, the physical dead space for a given size patient will be substantially minimized. The use of the pacifier attached to the face mask also helps properly orient the mask when placing it over the patients face. Additionally, with the presence of the pacifier in the oropharynx of the patient reduces the anatomical dead space. Finally, the pacifier is constructed to be easily attached to a face mask for pre-operative and operative procedures, and used with the attachable shield 14 for pre- and post-operative care.

Since certain changes may be made in the above product assembly without departing from the scope of the invention herein involved, it is intended that all matter contained in the above description or shown in the accompanying drawings shall be interpreted in an illustrative and not in a limiting sense.

What is claimed is:

1. An assembly for use in inducing anesthetic gas, said assembly comprising, in combination:

face mask means for extending over at least the nose and mouth of a wearer of said face mask so as to (a) tightly contact the face of the wearer in order to define a confined air space between said face mask means and the face of the wearer, (b) prevent the accumulation in said confined air space of an unacceptably large quantity of air exhaled by the wearer, and (c) permit the anesthetic gas to be introduced into the confined air space, said face mask means including an opening adapted to receive the gas;

an elongated, integrally-formed pacifier element including an orifice at one end thereof, a hole at the other end thereof and a passageway extending through said element from said orifice to said hole, and means for selectively attaching said pacifier element to said face mask means, so that said pacifier element is adapted to be inserted into the mouth of the wearer so as to occupy a substantial portion of the anatomical space of the oropharynx and depress the tongue of the wearer, and adapted to transmit gas received at said opening of said face mask means through said orifice, and into said passageway; and fragrance means, incorporated in said face mask means, for providing a predetermined fragrance.

2. An assembly according to claim 1, further including shield means for engaging the wearer's face adjacent the wearer's mouth and for detachably engaging said pacifier element when said pacifier element is detached from said face mask means.

3. An assembly according to claim 2, wherein said shield means is made of a predetermined material and said fragrance means is provided in said material.

4. An assembly according to claim 1, wherein said pacifier element includes wall means for defining said passageway so that said passageway is non-collapsible and said pacifier element includes at least one aperture formed in said wall means and communicating with said passageway and disposed so as to permit the gas to pass from the opening of said face mask means, through the passageway of the pacifier element and through said aperture into said confined air space of said mask so that the wearer can breath said gas through the nose.

5. An assembly according to claim 4, wherein said pacifier element includes a plurality of said apertures.

6. An assembly according to claim 4, wherein said aperture is disposed in said wall means of said pacifier element at a location between said orifice and said hole, said opening of said face mask means and said passageway being oriented with respect to one another when said pacifier element is attached by said attaching means to said face mask so that the end of a catheter can be inserted through said opening into said passageway and positioned between said aperture and said hole.

7. An assembly according to claim 4, wherein said attaching means includes a radial, inwardly-directed flange disposed at said opening of said face mask means and channel defining said disposed on said one end of said pacifier element for receiving said radial, inwardly-directed flange to secure said pacifier at said opening.

8. An assembly according to claim 7, wherein said channel defining means includes a radial, outwardly-directed flange and an outwardly-directed, resilient lip parallel to and spaced from said radial, outwardly-directed flange so as to define a channel, said pacifier element being adapted to slide to and from the exterior side of said face mask means through said opening so that said lip engages and is forced past said inwardly-directed flange when said pacifier element is secured to and removed from said face mask means.

9. An assembly according to claim 8, wherein said pacifier element further includes a groove formed in said pacifier element between said flange and said lip and opened outwardly into said channel for increasing the flexibility of said lip as it is forced past said inwardly-directed flange.

10. An assembly according to claim 7, further including shield means, wherein said pacifier element is adapted to be detachably secured to said shield means when detached from said face mask means, said shield means including an aperture sized so as to releasably engage said pacifier element when said shield means is secured in said channel defining means.

11. An assembly according to claim 10, wherein said shield means is made of a predetermined material and said fragrance means is provided in said material.

12. An assembly according to claim 1, wherein said fragrance means is incorporated in said pacifier element.

13. An assembly according to claim 12, wherein said pacifier element is formed of a plastic material and said fragrance means for providing a predetermined fragrance comprises a fragrance concentrate incorporated in said plastic material.

14. An assembly according to claim 1, wherein said face mask means is made of a predetermined material and said fragrance means is provided in said material.

15. A pacifier adapted to be secured to a face mask during pre-operative and operative procedures and detached and used separately from the face mask during pre- and post-operative care, said pacifier comprising:

(a) an integrally-formed elongated element including wall means having a base end defining an orifice, a tip end opposite said base end and defining a hole, a non-collapsible passageway extending through said element from said orifice to said hole, at least one aperture extending through said wall means into said passageway, and means for detachably securing said element to the face mask, said tip end being adapted to be positioned in the oropharynx of the user when the pacifier is used, said means for detachably securing said element including means for defining an outward, radially-directed channel circumferentially disposed around said element, wherein said channel defining means includes a radial, outwardly-directed flange and an outwardly-directed, resilient lip parallel to and spaced from said said radial, outwardly-directed flange so as to define a channel and said element further includes a groove formed in said element between said flange and said lip and opened outwardly into said channel for increasing the flexibility of said lip relative to said flange; and (b) fragrance means incorporated in said pacifier element for providing a predetermined fragrance.

16. A pacifier according to claim 15, wherein said element is formed from a plastic material and said fragrance means is disposed in said plastic material.

* * * * *

UNITED STATES PATENT AND TRADEMARK OFFICE
CERTIFICATE OF CORRECTION

PATENT NO. : 4,896,666

DATED : January 30, 1990

INVENTOR(S) : Allen J. Hinkle

It is certified that error appears in the above-identified patent and that said Letters Patent is hereby corrected as shown below:

Claim 1, column 6, line 5, after "mask" insert -- means --;

Claim 4, column 6, line 46, after "mask" insert -- means --;

Claim 6, column 6, line 56, after "mask" insert -- means --;

Claim 7, column 6, line 62, delete "said" (first occurrence) and substitute therefor -- means --;

Claim 15, column 8, line 14, delete "," and substitute therefor -- and --; and

Claim 15, column 8, line 21, delete "said" (first occurrence).

Signed and Sealed this

Twenty-ninth Day of January, 1991

*Attest:*

HARRY F. MANBECK, JR.

*Attesting Officer*  *Commissioner of Patents and Trademarks*